United States Patent [19]

Piselli

[11] Patent Number: 5,013,834
[45] Date of Patent: May 7, 1991

[54] PROCESS FOR THE PREPARATION OF AN OPTICALLY ACTIVE BENZOTHIAZEPINONE

[75] Inventor: Fulvio L. Piselli, Milan, Italy

[73] Assignee: Industria Chimica Profarmaco S. p. A., Milan, Italy

[21] Appl. No.: 527,029

[22] Filed: May 21, 1990

Related U.S. Application Data

[62] Division of Ser. No. 297,993, Jan. 17, 1989, Pat. No. 4,931,578.

[30] Foreign Application Priority Data

Jan. 28, 1988 [IT] Italy ............................... 19234 A/88

[51] Int. Cl.$^5$ .................... C07D 281/10; A61K 31/55

[52] U.S. Cl. ....................................... 540/491; 560/17; 562/401; 562/402; 562/431

[58] Field of Search .......................................... 540/491

[56] References Cited

U.S. PATENT DOCUMENTS 3,562,257  2/1971  Kugita et al. ...................... 540/491

Primary Examiner—Robert T. Bond
Attorney, Agent, or Firm—Walter H. Schneider

[57] ABSTRACT

A process for the optical resolution of 2-hydroxy-3-(4-methoxyphenyl)-3-(2-acetylaminophenylthio)-propionic acid sodium salt by seeding of a supersaturated solution of said salt with one of the enantiomers.

1 Claim, No Drawings

PROCESS FOR THE PREPARATION OF AN OPTICALLY ACTIVE BENZOTHIAZEPINONE

This application is a division of application Ser. No. 297,993 filed Jan. 17, 1989. Now U.S. Pat. No. 4,931,587.

The present invention relates to a process for the optical resolution of 2-hydroxy-3-(4-methoxyphenyl)-3-(2-acetylaminophenylthio)propionic acid of formula (I):

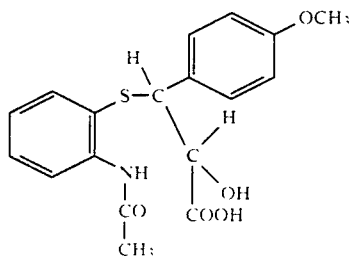

wherein the 3-(2-acetylaminophenylthio) and 2-hydroxy groups are in the "E" form. Compound (I) is an useful intermediate for the synthesis of optically active benzothiazepines, particularly of 2S-cis-5-[2-(dimethylamino)ethyl]-2,3-dihydro-3-hydroxy-2-(p-methoxyphenyl)-1,5-benzothiazepin-4(5H)-one of formula (II):

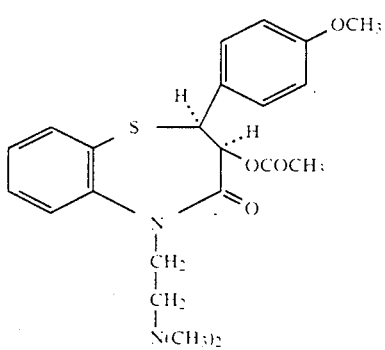

which is known to have coronaro-dilating activity.

Processes for the optical resolution of both the pharmacologically active compound (II) and the synthetic intermediates for the compound itself are described in literature. All these processes require optically active substances, which involves difficulties in availability, economy and quality.

Now, it has surprisingly been found, and it is the object of the present invention, that sodium salts of the racemic mixture comprising (2R,3R)-2-hydroxy-3-(4-methoxyphenyl)-3-(2-acetylaminophenylthio)propionic and (2S,3S)-2-hydroxy-3-(4-methoxyphenyl)-3-(2-acetylaminophenylthio)propionic acids, can be resolved with no use of optically active substances, by means of preferential crystallization through seeding of a supersaturated solution with one of the separated isomers of said salts.

Separation of the optical isomers is made possible by the known supersaturation phenomenon (see G. Amiard, Bull. Soc. Chim. Fr. 1956, 447; L. Velluz, G. Amiard, R. Hly, Bull. Chim. Fr. 1953, 903; G. Amiard, Experientia 1959, 15 38) of the two isomers present in the solution and by the subsequent preferential precipitation of one of them, till attainement of normal saturation conditions which take the system to balance conditions; supersaturation conditions are then restored by addition of an amount of racemic salt equivalent to the one obtained by crystallization.

From the resulting solution, after seeding, the opposite isomer to the previously obtained one will crystallize, in the same amount as the added racemic mixture. Repeating again, by the same procdure, the addition, seeding and crystallization cycles, amounts of the optical isomers of opposite sign will alternatively be obtained which are equal to the amounts of the used racemic derivative; the cycles can be repeated as many times as desired, without affecting yields and optical qualities.

The above mentioned acid racemic mixture will be hereinafter named "(2S,3S) (2R,3R) acid", for sake of shortness.

According to the invention, supersaturated solutions of the (2S,3S) (2R,3R) acid sodium salts can be obtained using as solvents lower alcohols or lower ketones which contain or do not varying water amounts. Methanol containing 2% to 4% water is particularly preferred.

Supersaturation conditions are reached at temperatures from above 40° C. to the solvent reflux temperature. Crystallization following seeding takes place at a temperature depending on the water content of the solvent mixture, which temperature is in principle from 18° to 45° C.; in the preferred case, crystallization is carried out at a temperature of about 27°-35° C.

The reaction can be effected either starting from previously prepared sodium salts or obtaining the same in situ treating the solution of the above acids with NaOH. Following the process of the invention, the optically pure dextrortatory salt of compound (I) is easily obtained from which the following compounds can be obtained:

(a) the corresponding acid, by simple treatment with mineral or organic acids to pH about 5; or
(b) by mild hydrolysis with mineral acids, (+)-2-hydroxy-3-(4-methoxyphenyl)-3-(2-aminophenylthio)propionic acid (2S,3S), of formula (III)

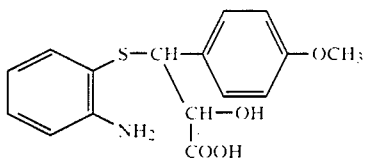

or (c) under slightly stronger conditions, benzothiazepine derivative of formula (IV)

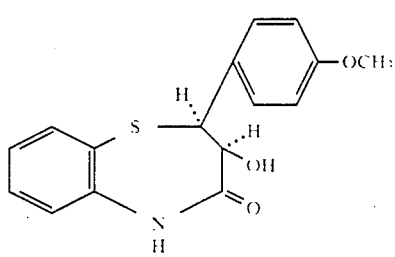

Hydrolysis as in point (b) above is generally carried out with diluted mineral acids, in an acid:water ratio of about 1:10–1:25 w/w. and in a mineral acid: acid (I) molar ratio between 1:1 and 5:1, at temperatures from 40° to 80° C. Cyclization (c), on the contrary, is effected by subjecting acid (I) to prolonged ebollition with 1–5 moles of mineral acid diluted in water in 1:25–1:50 ratio.

The present invention also relates to a process for a further purification of the sodium salts obtained by the above described resolution, by means of a treatment of said salts with methanol, at temperatures from room temperature to the reflux temperature of the mixture, which treatment is followed by filtration or centrifugation of the obtained suspension. Sodium salts of the (2S,3S)- and (2R,3R)-2-hydroxy-3-(4-methoxyphenyl)-3-(2-acetylaminophenylthio)propionic acids, in a high optical purity, are thereby isolated. Purification treatment is preferably carried out at the reflux temperature of the suspension, in sodium salt: methanol ratios from 1:5 to 1:20 w/v.

The following examples illustrate in more detail the process of the invention, but in no way limit the spirit and scope thereof.

EXAMPLE 1

(a)

2-hydroxy-3-(4-methoxyphenyl)-3-(2-acetylaminophenylthio)propionic acid methyl ester, racemic mixture (2S,3S)(2R,3R)

33.3 g (0.1 mole) of 2-hydroxy-3-(4-methoxyphenyl)-3-(2-acetylaminophenylthio)propionic acid methyl ester (racemic mixture) were dissolved in 70 ml of toluene at about 65° C. 10 g (0.1 mole) of acetic anhydride were added: the reaction was exothermic and temperature rose to about 85° C. After 60 minutes more at 80° C., the mixture was diluted with 25 ml of water and slowly neutralized with 5 g of $Na_2CO_3$.

The aqueous phase was decanted and the organic phase was cooled to 0° C., filtered and washed with toluene (20 ml). 33 g of the substantially pure compound were obtained. m.p.=209°–211° C. Yield: 88% on theory.

| Elementar analysis for $C_{19}H_{21}NO_5S$ | | | | |
|---|---|---|---|---|
|  | C | H | N | S |
| Calc. % | 60.77 | 5.64 | 3.72 | 8.54 |
| Found % | 60.77 | 5.68 | 3.74 | 8.51 |

IR Spectrum, $cm^{-1}$: 3550 (NH); 1730 ($COOCH_3$); 1680 (CONH).

(b)

2-hydroxy-3-(4-methoxyphenyl)-3-(2-acetylaminophenylthio)-propionic acid sodium salt, racemic mixture (2S,3S)(2R,3R)

37.5 g (0.1 mole) of 2-hydroxy-3-(4-methoxyphenyl)-3-(2-acetylaminophenylthio)propionic acid methyl ester, racemic mixture (2S,3S)(2R,3R), were dissolved in 100 ml of methanol containing 4 g (0.1 mole) of sodium hydroxide. The mixture was refluxed for about 60 minutes, then cooled to 0° C.; the obtained crystal compound was filtered and washed with 10 ml of iced methanol. After drying under vacuum at 60° C., 30 g of the racemic mixture were obtained. Yield: 78% on theory.

Mother liquors were recycled to hydrolyze again 0.1 mole of the methyl ester, using 4 g (0.1 mole) more of solid sodium hydroxide. Repeating the same procedure, 37 g of the same compound equal to that from the first cycle were obtained. Total yield on the two cycles: 87.5% on theory.

Alternatively, the sodium salt of the title can be obtained repeating the procedure as in point (a) until decanting the aqueous phase, thereafter the organic phase is extracted at 60° C. with a mixture of 10 ml of 10 N NaOH and 10 ml of methanol; the resulting hydroalcoholic basic layer is separated and treated with 100 ml of acetone. The desired sodium salt crystallizes which is filtered at 20° C., washed with acetone and dried under vacuum at 60° C. 35 g of the pure salt are obtained, equal to a 91% yield on theory.

(c) Resolution of the Racemic Mixture 90 g of the (2S,3S)(2R,3R) acid sodium salt were dissolved under reflux in 1 liter of methanol containing about 3% water; 10 g of (2S,3S)-2-hydroxy-3-(4-methoxyphenyl)-3-(2-acetylaminophenylthio)propionic acid sodium salt were added thereto and the mixture was cooled to about 40° C. 3 g more of (2S,3S)-2-hydroxy-3-(4-methoxyphenyl)-3-(2-acetylaminophenylthio)propionic acid sodium salt were added and the mixture was slowly stirred for 3–5 hours, slowly cooling to about 27°–30° C. The precipitate was filtered and washed with methanol (2×20 ml). 23 g of (2S,3S)-2-hydroxy-3-(4-methoxyphenyl)-3-(2-acetylaminophenylthio)propionic acid sodium salt were obtained, having a 85–87% optical purity. Mother liquors were added with 20 g of the (2S,3S)(2R,3R) acid sodium salt and refluxed to complete dissolution. The obtained solution was cooled to about 40° C., added with 3 g of (2R,3R)-2-hydroxy-3-(4-methoxyphenyl)-3-(2-acetylaminophenylthio)propionic acid and cooled under slow stirring to about 27°–30° C. Cystals were filtered and washed with 2×20 ml methanol. 23 g of (2R,3R)-2-hydroxy-3-(4-methoxyphenyl)-3-(2-acetylaminophenylthio)propionic acid sodium salt were obtained, having a 87% optical purity.

Mother liquors were added again with 20 g of (2S,3S)(2R,3R) acid sodium salt and refluxed to complete dissolution. The solution was cooled to about 40° C., added with 3 g of (2S,3S)-2-hydroxy-3-(4-methoxyphenyl)-3-(2-acetylaminophenylthio)propionic acid and left to cool to 27°–30° C. for 3–5 hours, under slow stirring. Crystals were filtered and washed with 2×20 ml methanol.

23 g of (2S,3S)-2-hydroxy-3-(4-methoxyphenyl)-3-(2-acetylaminophenylthio)propionic acid sodium salt were obtained, having an about 85% optical purity.

Mother liquors can be recycled as many times as desired, complying wiht the described procedures and the appropriate controls.

ANALYTIC CONTROLS (1) Methanol solution, before seeding, is checked at the pH-meter, diluting 2 ml of solution to a volume of 50 ml with distilled water. pH must be about 10.

(2) During crystallization of the enantiomer, a sample from filtered mother liquors is checked on polarymeter. Optimum crystallization takes place when $[\alpha]_D^{20} = 275° \pm 15°$ C. with a opposite sign to that of the growing crystal.

(3) 1 g of each 2-hydroxy-3-(4-methoxyphenyl)-3-(2-acetylaminophenylthio)propionic acid sodium salt enantiomer is dissolved in N/1 NaOH to a 100 ml volume at 20° C. The optical rotation is read in a 1 dm polarimetric tube.

$[\alpha]_D^{20} = 170° - 175°$.

The compound of 100% optical purity has an optical activity of $[\alpha]_D^{20°} = 200°$.

Alternatively to what described in Example 1, the hereinbelow procedure can be followed.

EXAMPLE 2

Racemic Mixture Resolution 84 g of (2S,3S)(2R,3R) acid (prepared as described in Example 4 for one of the enantiomers of the same acid) and 10 g of (2S,3S)-2-hydroxy-3-(4-methoxyphenyl)-3-(2-acetylaminophenylthio)propionic acid were dissolved in 1 liter of methanol containing 3% water, at about 40° C. The mixture was alkalinized by dropping 105 ml of 10% NaOH in methanol w/v, to pH 10.

The obtained solution was seeded with 3 g of (2S,3S)-2-hydroxy-3-(4-methoxyphenyl)-3-(2-acetylaminophenylthio)propionic acid sodium salt and the mixture was stirred for about 3-5 hours at 27°-35° C. The separated crystal precipitate was filtered and washed with 20 ml of methanol. 23 g of (2S,3S)-2-hydroxy-3-(4-methoxyphenyl)-3-(2-acetylaminophenylthio)propionic acid was obtained, having about 87% optical purity. Mother liquors were added with 20 g of (2S,3S)(2R,3R) acid and 22 ml of 10% (w/w) NaOH in methanol. The solution was seeded with 3 g of (2R,3R)-2-hydroxy-3-(4-methoxyphenyl)-3-(2-acetylaminophenylthio)propionic acid sodium salt and crystals were left to grow at about 27°-30° C. for about 3-5 hours, then filtered and washed with about 20 ml methanol.

23 g of (2R,3R)-2-hydroxy-3-(4-methoxyphenyl)-3-(2-acetylaminophenylthio)propionic acid sodium salt were obtained, having an about 85% optical purity.

Mother liquors were treated again according to the same procedure, adding racemic acid portions, to alternatively obtain equal amounts of the dextro- and laevo-rotatory isomers.

Analytic controls were carried out as described in Example 1.

EXAMPLE 3

Purification of (2S,3S)-2-hydroxy-3-(4-methoxyphenyl)-3-(2-acetylaminophenylthio)propionic acid sodium salt 25 g (0.065 mol) of (2S,3S)-2-hydroxy-3-(4-methoxyphenyl)-3-(2-acetylaminophenylthio)propionic acid sodium salt having an approximately 80% optical purity were refluxed for 60 minutes in 250 ml of methanol, then cooled to about 20° C., filtered and washed with 10 ml of methanol.

19 g of compound was obtained, having a ≧90% optical purity.

The same procedure was carried out using the (−) enantiomer sodium salt, with an optical purity of about 80%. 19 g of compound having a ≧90% optical purity were obtained.

Mother liquors from the two treatments were combined and evaporated to small volume; the crystallizate was filtered to recover 12 g of substantially racemic sodium salt.

EXAMPLE 4

(2S,3S)-2-hydroxy-3-(4-methoxyphenyl)-3-(2-acetylaminophenylthio)propionic acid 78 g of (2S,3S)-2-hydroxy-3-(4-methoxyphenyl)-3-(2-acetylaminophenylthio)propionic acid sodium salt with ≅90% optical purity were dissolved in 750 ml of water. 12 g of acetic acid were dropped therein to pH about 5. The mixture was left to crystallize for about 60 minutes, filtered and washed with 100 ml of water.

59 g of (2S,3S)-2-hydroxy-3-(4-methoxyphenyl)-3-(2-acetylaminophenylthio)propionic acid were obtained, with optical purity 98-100%. M.p. 173°-175° C.

From mother liquors, upon acidification with 20 ml of 32% (w/w) hydrochloric acid, 13 g of substantially racemic acid precipitated.

Following Examples 5 and 6 relate to cyclization of the enantiomer which had been isolated according to the invention to benzothiazepine derivative (IV) and to the deacetalization thereof to acid (III), respectively.

EXAMPLE 5

2S-cis-hydroxy-2,3-dihydro-2-(4-methoxyphenyl)-1,5-benzothiazepin-4-(5H)-one (IV)

90 g (0.25 mol) of (2S,3S)-2-hydroxy-3-(4-methoxyphenyl)-3-(2-acetylaminophenylthio)proionic acid (obtained according to Example 4) were suspended in 300 ml of water, containing 25 ml of 32% (w/w) hydrochloric acid in the presence of 1 g of KI. The mixture was heated to mild reflux for about 20 hours, the suspension was cooled to about 20° C. and filtered, washing the precipitate with water.

65 g of 2S-cis-hydroxy-2,3-dihydro-2-(4-methoxyphenyl)-1,5-benzothiazepin-4-(5H)-one were obtained, upon drying at 60° C. in vacuum. M.p. 206°; $[\alpha]_{20}^D = 106°$ (c = 1% in dioxane-methanol 30:70).

EXAMPLE 6

(2S,3S)-2-hydroxy-3-(4-methoxyphenyl)-3-(2-aminophenylthio)propionic acid (III)

60 g (1.65 mol) of (2S,3S)-2-hydroxy-3-(4-methoxyphenyl)-3-(2-acetylaminophenylthio)propionic acid were suspended in 300 ml of water containing 50 ml of 32% (w/w) hydrochloric acid in the presence of 0.5 g of KI. The mixture was heated to slow reflux for about 3 hours, filtered at about 80° C., separating approximatively 10 g of unsolubles, and the filtered waters were neutralized to pH 6 with 30% (w/w) NaOH, cooled to about 15° C., filtered and thoroughly washed with water. 36 g of (2S,3S)-2-hydroxy-3-(4-methoxyphenyl)-3-(2-aminophenylthio)propionic acid were obtained with 80% optical purity 98-100%. The acid pH hot filtered unsolubles consisted of a mixture of non unhydrolyzed compound and of compound cyclized to benzothiazepine ring.

I claim:

1. A process for the preparation of 2S-cis-hydroxy-2,3-dihydro-2-(4-methoxyphenyl)-1,5-benzothiazepin-4-(5H)-one, in which (2S,3S)-2-hydroxy-3-(4-methoxyphenyl)-3-(2-acetylaminophenylthio)propionic acid (I) is subjected to prolonged ebollition with 1 to 5 moles of mineral acid which is diluted with water in 1:25 to 1:50 ratios.

* * * * *

UNITED STATES PATENT AND TRADEMARK OFFICE
CERTIFICATE OF CORRECTION

PATENT NO.   : 5,013,834
DATED        : May 7, 1991
INVENTOR(S)  : Fulvio L. Piselli It is certified that error appears in the above-identified patent and that said Letters Patent is hereby corrected as shown below:

On the Title page, Item [62], "Pat No. 4,931,578 should read ---Pat. No. 4,931,587---

Signed and Sealed this

Second Day of March, 1993

Attest:

STEPHEN G. KUNIN

Attesting Officer

Acting Commissioner of Patents and Trademarks